(12) United States Patent
Langhoff et al.

(10) Patent No.: US 9,407,836 B2
(45) Date of Patent: Aug. 2, 2016

(54) ELECTRONIC X-RAY CAMERA WITH SPECTRAL RESOLUTION

(75) Inventors: Norbert Langhoff, Berlin (DE); Aniouar Bjeoumikhov, Berlin (DE); Heike Soltau, München (DE); Robert Hartmann, Gröbenzell (DE)

(73) Assignees: PNSensor GmbH, Munich (DE); IFG-Institute for Scientific Instruments GmbH, Berlin (DE)

( * ) Notice: Subject to any disclaimer, the term of this patent is extended or adjusted under 35 U.S.C. 154(b) by 599 days.

(21) Appl. No.: 13/126,192

(22) PCT Filed: Oct. 27, 2009

(86) PCT No.: PCT/EP2009/064125
§ 371 (c)(1),
(2), (4) Date: Jul. 14, 2011

(87) PCT Pub. No.: WO2010/049409
PCT Pub. Date: May 6, 2010

(65) Prior Publication Data
US 2011/0293068 A1    Dec. 1, 2011

(30) Foreign Application Priority Data

Oct. 27, 2008  (DE) .......................... 10 2008 053 821
Feb. 16, 2009  (DE) .......................... 10 2009 009 602

(51) Int. Cl.
*H04N 5/32*     (2006.01)
*H05G 1/64*     (2006.01)
*G01T 1/36*     (2006.01)
*G01N 23/207*   (2006.01)

(52) U.S. Cl.
CPC ............. *H04N 5/32* (2013.01); *G01N 23/2076* (2013.01); *G01T 1/36* (2013.01)

(58) Field of Classification Search
CPC ....... H04N 5/32; G21K 7/00; G01N 23/2076; G01T 1/36
USPC .......................................................... 378/43
See application file for complete search history.

(56) References Cited

U.S. PATENT DOCUMENTS 3,772,521 A    11/1973  Perez-Mendez
4,515,439 A *   5/1985  Esswein ........................ 359/381
(Continued)

FOREIGN PATENT DOCUMENTS

DE    37 35 296 A1    4/1989
DE    10303438        10/2003
(Continued)

OTHER PUBLICATIONS

Porro et al. "A new silicon detector system for optical and low light imaging, based on DEPFER RNDR." 2007. IEEE.*
(Continued)

*Primary Examiner* — David J Makiya
*Assistant Examiner* — Dani Fox
(74) *Attorney, Agent, or Firm* — Walter Ottesen, P.A.

(57) ABSTRACT

An X-ray camera includes a camera housing, an image pickup element which is sensitive at least for X-rays, and an X-ray objective. The X-ray objective lens has a capillary structure and the image pickup element is constructed as a two-dimensional pixilated semiconductor sensor for simultaneous spatial, energy and time resolution.

23 Claims, 4 Drawing Sheets

(56) References Cited

U.S. PATENT DOCUMENTS

| | | | |
|---|---|---|---|
| 5,216,250 A * | 6/1993 | Pellegrino et al. | 250/370.09 |
| 5,357,110 A * | 10/1994 | Statham | G01N 23/223 |
| | | | 250/307 |
| 5,491,738 A | 2/1996 | Blake et al. | |
| 5,584,292 A * | 12/1996 | Cheung | 600/567 |
| 5,600,701 A * | 2/1997 | Baba et al. | 378/98.2 |
| 5,719,401 A * | 2/1998 | Chaney et al. | 250/370.1 |
| 6,205,199 B1 * | 3/2001 | Polichar et al. | 378/98.8 |
| 6,233,306 B1 * | 5/2001 | Van Sprang | 378/35 |
| 6,442,236 B1 * | 8/2002 | Utaka | 378/84 |
| 6,533,641 B1 * | 3/2003 | Morken et al. | 451/6 |
| 6,859,516 B2 * | 2/2005 | Schneider et al. | 378/43 |
| 6,962,289 B2 * | 11/2005 | Vatan et al. | 235/462.01 |
| 6,994,747 B2 * | 2/2006 | Hiraiwa et al. | 117/13 |
| 6,996,207 B2 * | 2/2006 | Kumakhov | 378/43 |
| 7,081,962 B2 * | 7/2006 | Nakauchi | 356/521 |
| 7,550,811 B2 * | 6/2009 | Kobayashi et al. | 257/431 |
| 2001/0046276 A1 * | 11/2001 | Schneider et al. | 378/58 |
| 2002/0196899 A1 * | 12/2002 | Karellas | 378/98.8 |
| 2003/0019932 A1 * | 1/2003 | Tsikos et al. | 235/454 |
| 2003/0142781 A1 * | 7/2003 | Kawahara et al. | 378/44 |
| 2004/0264631 A1 * | 12/2004 | Joshi et al. | 378/19 |
| 2005/0006588 A1 * | 1/2005 | Fuchs et al. | 250/367 |
| 2005/0276379 A1 * | 12/2005 | Polichar et al. | 378/98.2 |
| 2006/0086794 A1 * | 4/2006 | Knowles et al. | 235/454 |
| 2006/0194334 A1 * | 8/2006 | Zhang | 436/172 |
| 2006/0240586 A1 * | 10/2006 | Kobayashi et al. | 438/26 |
| 2006/0261278 A1 * | 11/2006 | Accorsi | 250/363.06 |
| 2007/0041492 A1 | 2/2007 | Sakurai et al. | |
| 2008/0080614 A1 * | 4/2008 | Munoz et al. | 375/240.01 |
| 2008/0128631 A1 * | 6/2008 | Suhami | 250/370.09 |
| 2008/0159479 A1 | 7/2008 | Huang | |
| 2008/0191123 A1 * | 8/2008 | Lutz et al. | 250/208.1 |
| 2008/0197290 A1 * | 8/2008 | Yuan et al. | 250/370.11 |

FOREIGN PATENT DOCUMENTS

| | | |
|---|---|---|
| DE | 10 2005 025 641 A1 | 12/2006 |
| EP | 0 421 632 A2 | 4/1991 |
| EP | 0 667 540 B1 | 8/1995 |
| EP | 1953537 | 8/2008 |
| EP | 2 377 309 B1 | 10/2011 |
| WO | WO2007/019053 | 2/2007 |

OTHER PUBLICATIONS

International Search Report dated Feb. 18, 2010.

Arkadiev, V.A. et al, "X-ray focusing by polycapillary arrays", SPIE vol. 2515, 1995, pp. 514 to 525.

Bzhaumikhov, A.A. et al, "Polycapillary Conic Collimator for Micro-XRF", SPIE, vol. 3444, Jul. 1998, pp. 430 to 435.

Muradin A. Kumakhov: "X-ray capillary optics: history of development and present status", Proceedings of SPIE, vol. 4155, Jun. 8, 2000, pp. 2-12, XP055111442, ISSN: 0277-786X, DOI: 10.1117/12.387859.

XP055111464, Robert A. Austi Robert A. Austin et al: "High-pressure gas-scintillationproportional counter for the focus of a hard-x-ray telescope", Proceedings of SPIE, vol. 3765, Oct. 22, 1999, pp. 714-720.

XP055147056, Dale E. Newbury Dale E. Newbury: "The New X-ray Mapping: X-ray Spectrum Imaging above 100 kHz Output Count Rate with the Silicon Drift Detector", Microscopy and Microanalysis, vol. 12, No. 01, Jan. 24, 2006, pp. 26-35.

Lechner P. et al. "X-ray imaging spectrometers in present and future satellite missions," Nuclear Instruments & Methods in Pysics Research, Section A: Accelerators, Spectrometers, Detectors, and Associated Equipment, Elsevier BV, Bd. 509, Nr. 1-3, 21, Aug. 21, 2003, Seiten 302-314.

D.E. Newbury, "The new x-ray mapping: x-ray spectrum imaging above 100 kHz output count rate with silicon drift detector," Gefunden im Internet, Bd. 12, Nr. 01. Feb. 2006, Seiten 26-35.

Kemna A. et al. "Low noise, large area CMOS x-ray image sensor for CT application," Proceedings of IEEE Sensors 2003 (IEEE Cat. No. 03CH37498), Bd. Conf. 2, 22 Oct. 22, 2003, Seite 1260, XP010690979.

* cited by examiner

ELECTRONIC X-RAY CAMERA WITH SPECTRAL RESOLUTION

CROSS-REFERENCES TO RELATED APPLICATIONS

This application is the U.S. National Stage of International Application No. PCT/EP2009/064125, filed Oct. 27, 2009, which designated the United States and has been published as International Publication No. WO 2010/049409 and which claims the priority of German Patent Applications, Serial No. 10 2008 053 821.3, filed Oct. 27, 2008, and Serial No. 10 2009 009 602.7, filed Feb. 16, 2009, pursuant to 35 U.S.C. 119(a)(d).

BACKGROUND OF THE INVENTION

The invention relates to an x-ray camera, a use of the x-ray camera and a method for recording x-ray images with the features defined in the preambles of respective independent claims.

Sine the discovery of x-rays by Wilhelm Conrad Röntgen, different physical effects and methods have been used for detecting this very short wavelength radiation. This goes from detecting x-ray radiation with photographic films via ionization detectors and semiconductor detectors to modern x-ray cameras using luminophores and CCD arrays. This development was in particular advanced by medical diagnostic applications. A similar trend has been observed over the past decades in x-ray analytics, where other physical and technical boundary conditions had to be considered with respect to the x-ray photon energies, the energy resolution and the intensity. During the past 20 years, a trend for transitioning from compact single detector systems to spatially resolved detectors has occurred in both x-ray fluorescence spectroscopy and x-ray diffractometry. Initially, line cameras were preferably used, whereas during the past 10 years also area detectors have increasingly been employed. These detection systems are limited to detecting spatial information, i.e., individual pixels, which can form the basis for image representation, as well as detecting the intensity of the radiation for a single point (pixel).

The object of this patent is the physical and technical description of a novel x-ray color camera, which makes possible simultaneous spatial, energy and time resolution by using compact x-ray optics and a two-dimensional pixilated semiconductor sensor.

A two-dimensional image pickup element which is sensitive to x-rays and is structured across an area was for a long time only photo-chemically sensitized coated films and more recently also semiconductor chips, like an XMM-Newton or Chandra in x-ray telescopes orbiting the earth.

The radiation in non-image-forming radiation measurement devices (scintillation sensor, whole body counter or counting tube) is frequently collimated by simple conical tubes or lamellae. In a gamma camera, the collimator quasi resembles a perforated board, wherein the individual "holes" are separated by the so-called septa. These septa ensure that only the perpendicular rays can pass through the collimator, whereas photons incident at an angle are absorbed. The length of the septa which corresponds to the overall height of the collimator, and the width of the septa determine suitability for different photon energies (low-energy, medium-energy, high-energy and ultrahigh-energy). The sensitivity (measurement yield) depends on the ratio of hole width to the septa width. The channel ratio (septa length to hole width) determines the permissible entrance angle and hence the spatial resolution, which is therefore limited by the septa thickness (required for the respective photon energy). Collimators therefore generally always require a compromise between, on the one hand, the sensitivity and, on the other hand, the resolution. The resolution increases with a smaller width and greater length of the bores which, however, reduces the sensitivity, and vice versa.

The parallel-hole collimators produce a parallel projection. The measurement yield is almost independent of the distance to the object; however, the spatial resolution deteriorates significantly with increasing distance to the detector. Parallel-hole collimators are hexagonally folded and soldered either from lead or tungsten sheets, or are drilled into a solid block, or cast. The bores are preferably filled with a plastic material transparent for the radiation. Slant-hole collimators are parallel-hole collimators with inclined bores and enable, for example, measurements at the shoulders closer to the head of a patient. Diverging collimators produce an enlarged image. In fan-beam collimators, the holes only diverge in one spatial direction. This increases the counting yield, because a larger crystal region receives the radiation originating from a small object.

The known pinhole collimators operate according to the principle of the pinhole camera: a single "pupil" produces a reversed and inverted image, with the magnification of the image depending strongly on the object distance. Pinhole cameras are used to image particularly small radiating objects (wrist bones, test animals, potentially also thyroid), because they allow a strong magnification compared to the aforementioned collimators. More recently, multi-pinhole collimators are used which increases sensitivity without decreasing the spatial resolution.

Spatially sensitive detectors for x-ray radiation are known since some time. U.S. Pat. No. 3,772,521 "Radiation camera and delay line readout" describes such detector wherein a proportional counter is equipped with anode and cathode wire grids. An electrical signal is generated by the incident x-ray photons, which is localized depending on the position by the respective readout wire grid from the corresponding time delay of the signal transmission. An improved version of such detection system is described, for example, in the published patent application DE 37 35 296 A1 "Two-dimensional proportional counter for spatially sensitive measurement of ionizing radiation."

In addition, luminescent foils and storage foils are used as position-resolving detectors. These systems and the corresponding required readout devices are described, for example, in the patents EP 0421632 A2 "Digital x-ray image processing apparatus and method" and EP 0667540 B1 "Readout device for photo-stimulated information carriers". However, these detectors are not as powerful as CCD detectors, which have significantly better characteristics with respect to both the readout speed as the spatial resolution. Such detector systems, which are used particularly for diffractometric image recordings in crystallography, are in existence since the development in the late 80s of the 20th century. However, these detection systems only register intensity differences, i.e., they have only spatial resolution.

U.S. Pat. No. 5,491,738 describes an x-ray diffractometer and US 2007/0041492 A1 an x-ray diffractometer microscope, wherein both solutions each have an x-ray source as well as an x-ray detector. None of the solutions includes x-ray capillary optics or a two-dimensional pixilated x-ray detector.

A pn-CCD detector structure which can be used for the x-ray color camera according to the invention was described in the patent application DE 10 2005 025 641 A1.

Poly-capillary structures are to be used as optical systems, which are formed as parallel structures or conical structures. The following publications from the year 1995: V. A. Arkadiev, A. Bzhaumikhov: "X-ray focusing by polycapillary arrays", Proceedings of SPIE Vol. 2515 (1995) 514-525.) and from the year 1998: A. A. Bzhaumikhov, N. Langhoff, J. Schmalz, R. Wedell, V. I. Beloglazov, N. F. Lebedev: "Polycapillary conic collimator for micro-XRF", Proceedings of SPIE Vol. 3444 (1998) 430-435 address this subject. Unlike the aforedescribed x-ray collimators for hard x-rays made from lead or tungsten, the poly-capillary structures made from glass do not significantly absorb the low-energy x-ray radiation for which they are designed, but instead produce a reflection which essentially deflects the low-energy x-ray radiation.

EP 1953537 A1 describes a device for measuring and/or guiding x-ray radiation by using an x-ray optics, wherein the x-ray optics has capillaries. This x-ray optics is used for measuring and guiding the x-ray radiation, but not for generating images. The employed x-ray detector lacks any spatial resolution.

It is an object of the invention to provide a practical electronic x-ray camera capable of capturing in a simple manner images having spatial and spectral resolution, realizing different image modes and hence a simultaneous spectral recording of low-energy x-ray radiation at each image pixel.

SUMMARY OF THE INVENTION

According to a device aspect, the present invention is based on an x-ray camera having a camera housing, a pixilated image pickup element which is sensitive to x-rays and has a two-dimensional structure, and an x-ray objective.

According to a device aspect, the objects of the present invention are solved in that the x-ray objective (10) is configured has a capillary structure and the image pickup element is constructed as a two-dimensional pixilated semiconductor sensor for simultaneous spatial, energy and time resolution, for example a pn-CCD (Charge Coupled Device) or a monolithic two-dimensional SDD-field (silicon drift detector) or a DEPFET-macro-pixel field. In particular, a pn-CCD is capable of simultaneously capturing and spectroscopically analyzing the respective position-related x-ray radiation with each of the plurality of image pixel sensors arranged on the pn-CCD. This obviates the need for sequentially scanning an image point-by-point with only a single sensor which would prolong the radiation acquisition process. The employed pn-CCD image sensor has a high intensity resolution so that both the number of incident single photons and their energy can be measured.

The x-ray camera according to the invention attains additional advantages by being equipped with a camera shutter, which may be manually actuatable or with an electronic control.

The total intensity of the x-ray radiation incident on the camera for an image can be particularly advantageously adjusted by providing the x-ray camera with an aperture, wherein the aperture opening is predetermined and/or can be predetermined.

The x-ray objective has preferably an objective housing in which a capillary structure for the x-rays is arranged. In preferred embodiments, this capillary structure is constructed as a parallel-focusing collimator or a magnifying-focusing or reducing-focusing collimator.

The x-ray camera according to the invention can be particularly easily manipulated if the x-ray objective has a beam entry opening and a beam exit opening, wherein each opening is sealed gas-tight by a window which is transparent for low-energy x-ray radiation. The interior space of the x-ray objective is preferably filled with a gas. The gas prevents the formation of water condensate and/or icing. A suitable gas is nitrogen or helium or a gas mixture of both.

To ensure an advantageous exchangeability of the x-ray objectives, the x-ray objective is connected with the camera housing preferably via a releasable threaded lock or a bayonet lock.

According to another preferred embodiment of the x-ray camera according to the invention, the camera housing is constructed gas-tight and has a beam entrance opening, which is sealed gas-tight with a camera window that is transparent for low-energy x-ray radiation. The camera window prevents leakage of the enclosed gas, with which also the interior space of the camera housing is filled in a preferred embodiment of the present invention. In this embodiment, as previously for the x-ray objective, nitrogen or helium, or a gas mixture of both, is advantageously used as the gas.

The image pickup element of the x-ray camera according to the invention is cooled by a cooling device to a temperature in a range from +20° C. to −60° C., which corresponds to the operating temperature of the image pickup element, wherein the cooling device is embodied as a Peltier element. The Peltier element can be particularly easily electrically controlled. The warm side of the Peltier element transfers the dissipated heat to the rear wall of the housing, on which preferably at least one heat exchanger with or without a blower is arranged.

At least one of the windows of the x-ray objective and/or the camera window is preferably made of a material that is particularly transparent for low-energy x-ray radiation, such as beryllium or a polymer foil.

The x-ray camera according to the invention has in another preferred embodiment a preferably digital data storage device for storing recorded image data, wherein the data storage device is arranged inside or outside the camera housing.

To enable further processing of the recorded image data, the x-ray camera according to the invention has advantageously also a data transmission interface configured for data exchange with an external image processing device, in particular a computer.

According to a technical use aspect, the objects of the present invention are furthermore solved with an x-ray camera according to one of the aforedescribed embodiments for generating monochromatic and/or spectrally multi-colored digital x-ray image recordings.

According to another method-related aspect of the present invention, the present invention is based on a method for recording two dimensional spatially resolved images in a low-energy x-ray radiation range with at least one image pickup element sensitive for x-ray radiation, wherein the image pickup element has a plurality of ordered image pixel sensors.

The objects of the invention are solved by the method-related aspect of the present invention in that with each image pixel sensor a single photon capture and a determination of the associated photon energy of the x-ray radiation incident on the image pixel sensor is performed. According to another embodiment of the method according to the invention, a radiation spectrum of the x-ray radiation incident on the respective individual image pixel sensors is determined based on a single photon capture and the determination of the photon energy. In this way, the wavelength and the associated intensity of the incident x-ray radiation is measured at the position of each image pixel sensor.

The method according to the invention preferably uses a two-dimensional pixilated image pickup element sensitive for the x-ray radiation, such as a pn-CCD or a monolithic SDD-field or a DEPFET-macro-pixel field. To provide an example, a pn-CCD with about 256×256 pixels and a pixel size of about 50×50 $\mu m^2$ can be used in the x-ray camera according to the invention.

Additional preferred embodiments of the invention can be inferred from the other features recited in the dependent claims.

BRIEF DESCRIPTION OF THE DRAWING

Exemplary embodiments of the invention will now be described with reference to the appended drawings. These show in.

DETAILED DESCRIPTION OF PREFERRED EMBODIMENTS

Figure 1:
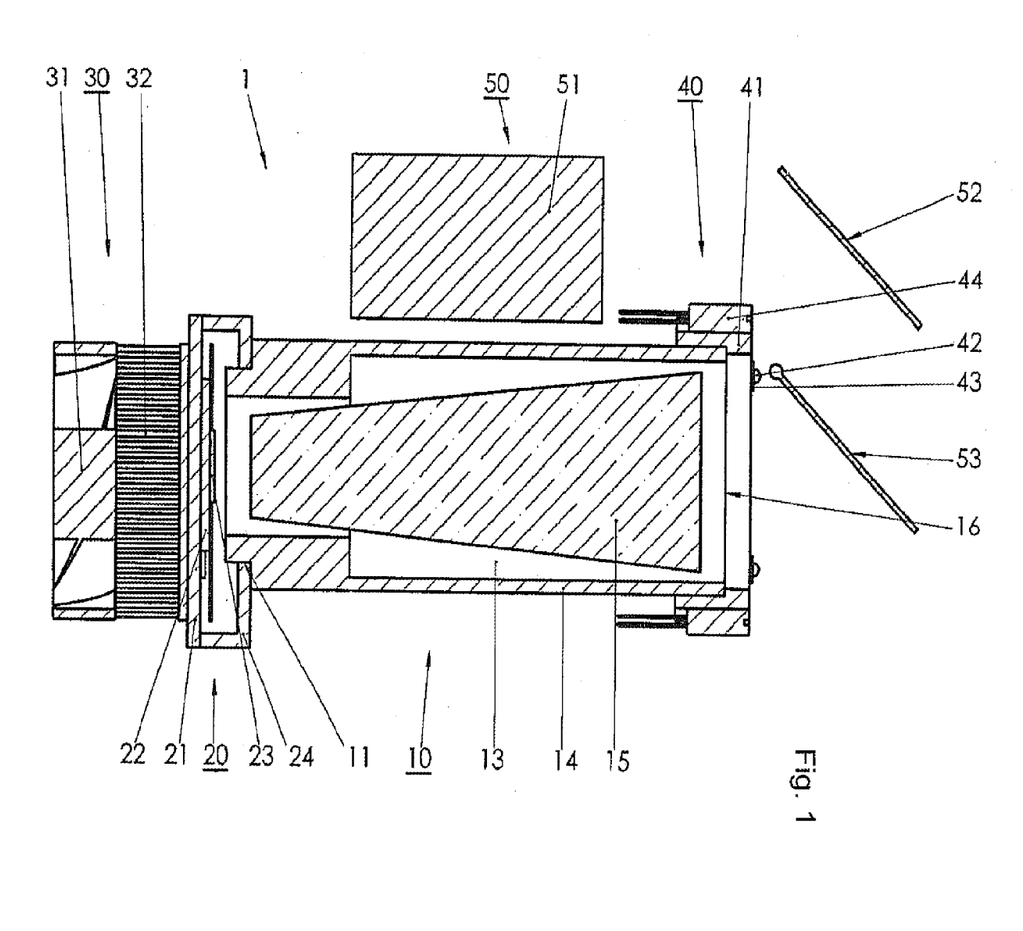
FIG. 1 a schematic cross-sectional view of an embodiment of an x-ray camera according to the invention.

FIG. 1 shows a schematic cross-sectional view of an embodiment of an x-ray camera 1 according to the invention. The x-ray camera 1 has a camera housing 20 and an x-ray objective 10. The camera housing 20 and the x-ray objective 10 are preferably releasably connected with one another via a threaded lock or a bayonet lock, thereby allowing simple exchangeability of the x-ray objective 10. The x-ray objective 10 has an objective housing 14, in which a capillary structure 15 is arranged. The capillary structure 15 has in the present embodiment a tapered configuration and corresponds in this configuration to a reducing focusing collimator.

Arranged in the camera housing 20 are an image pickup element or image sensor 23 and behind the image sensor 23 a Peltier element 22 operating as a cooling element. The Peltier element 22 is provided to cool the image pickup element 23 to a temperature near room temperature. The interior space of the camera housing 20 is preferably filled with an inert gas, such as helium or nitrogen, to prevent icing.

In the following embodiment, the rear wall of the camera housing 20 is additionally occupied by a cooling device 30. This cooling device 30 has a heat exchanger 32 and a blower 31. The x-ray radiation enters the x-ray objective 10 through a beam entrance opening 16 arranged on the front end of the x-ray objective 10 and from there into the collimator 15. A portion of the incident x-ray radiation which propagates along the capillary openings of the collimator 15 reaches the beam entrance opening 25 of the camera housing and impinges on the image pickup element 23.

Figure 2:
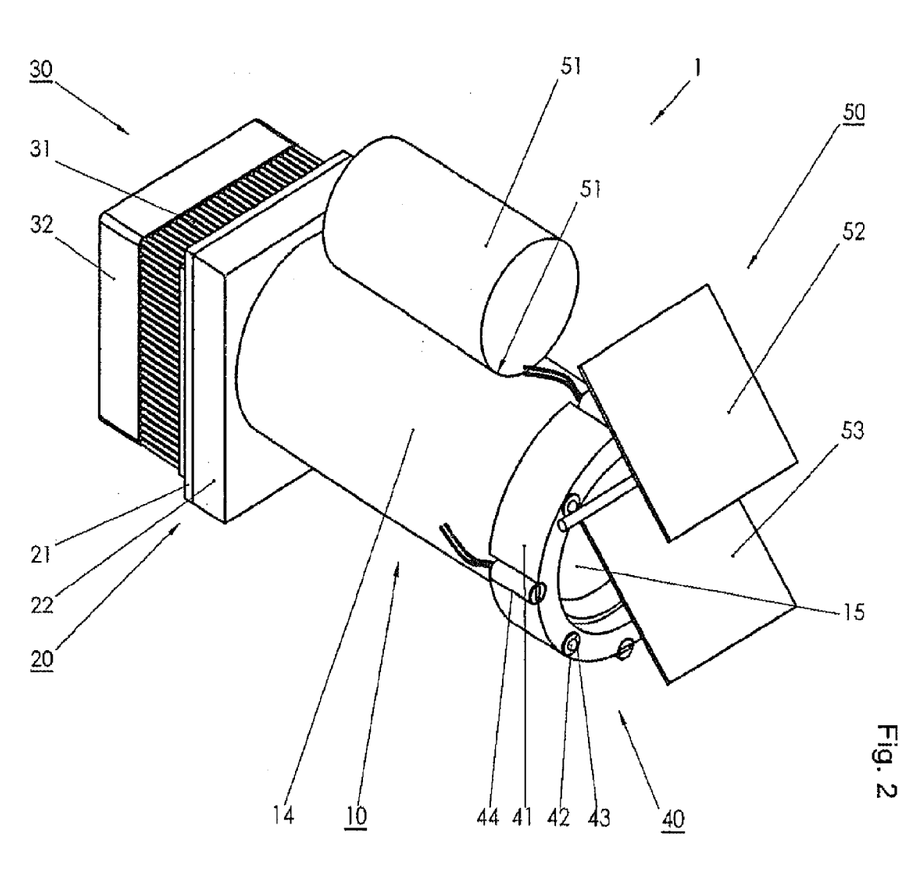
FIG. 2 a schematic perspective view of the embodiment of the x-ray camera according to the invention.

FIG. 2 shows schematically a perspective view of the embodiment of the x-ray camera 1 according to the invention of FIG. 1.

Figure 3:
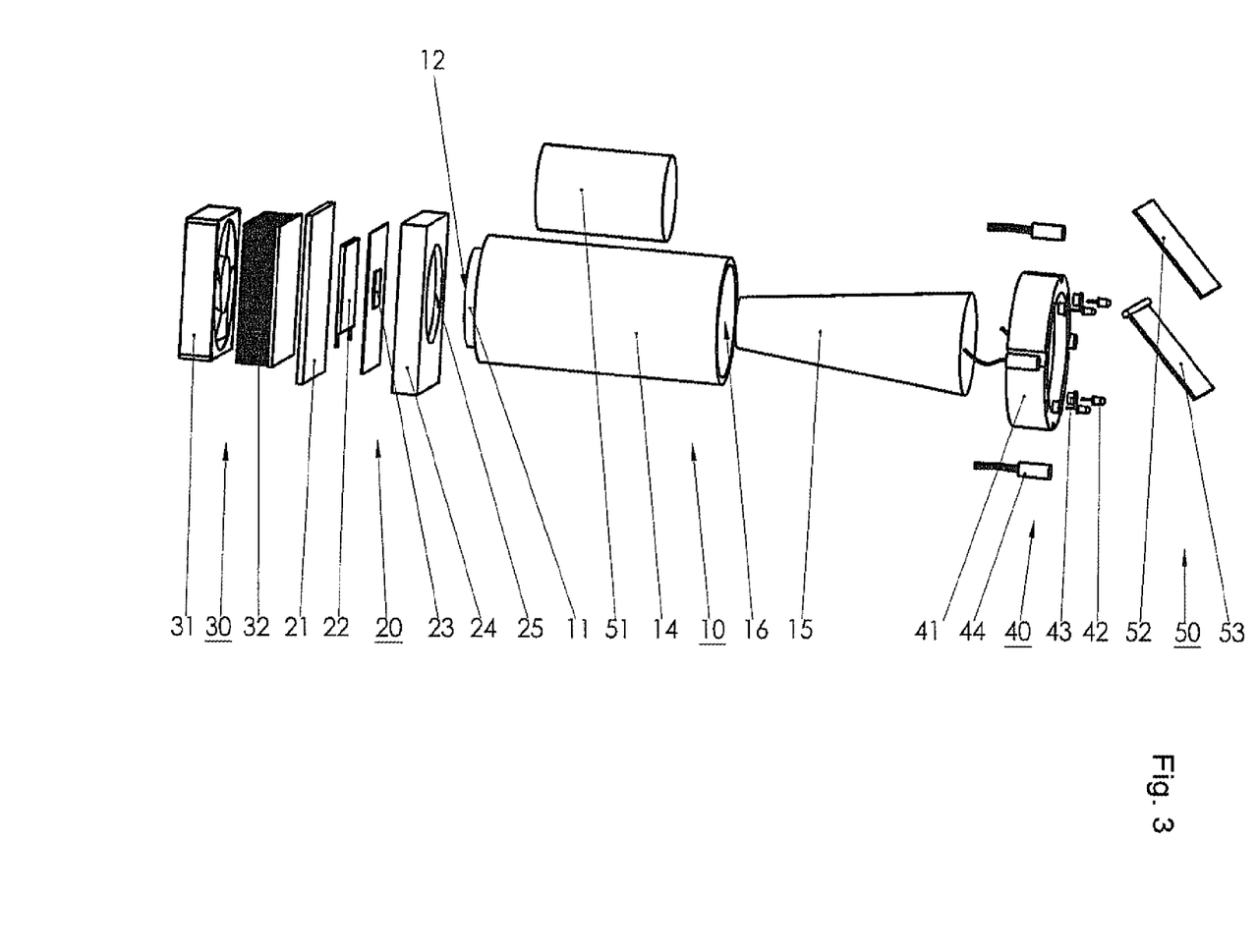
FIG. 3 a schematic exploded view of the embodiment of the x-ray camera according to the invention.

FIG. 3 shows schematically an exploded view of the embodiment of the x-ray camera 1 according to the invention of the FIGS. 1 and 2.

In sequential order from left to right, there are shown a blower 31 disposed on the heat exchanger 32, a housing rear wall 21, a Peltier element 22, an image pickup element 23, a housing shell 24 with a beam entrance opening 25, an objective housing 14 and a collimator 15. A threaded lock or a bayonet lock 11 of the objective housing 14 is schematically illustrated.

The image pickup element 23 is visible as a rectangular element and is according to the invention a pn-CCD semiconductor chip which has, for example, about 256×256 individual image recording pixels with a pixel size of, for example, 50×50 $\mu m^2$. The preferably employed pn-CCD semiconductor image sensor has preferably two integrated recording modules and uses preferably extremely fast-acting avalanche amplifiers for signal amplification.

In a preferred embodiment of the present invention, the camera housing 20 is filled with nitrogen or helium to prevent icing due to residual water molecules inside the housing. To make the x-ray objective 10 detachable from the camera housing 20 by a threaded lock or a bayonet lock, a window (not shown) which is transparent for the low-energy x-ray radiation is arranged on the beam entrance opening 25 on the camera housing. This window is constructed, for example, from beryllium or a polymer foil.

FIG. 3 shows a schematic exploded view of the embodiment of the x-ray camera according to the invention of FIGS. 1 and 2. The interior space 13 of the x-ray objective 10 includes in the present example a reducing focusing collimator 15. For the same reason as for the camera housing 20, the interior space 13 of the x-ray objective 10 is filled with nitrogen or helium to prevent icing due to residual water inside the housing.

To prevent the gas filling in the interior space 13 of the x-ray objective 10 from escaping when the x-ray objective 10 is exchanged, both the beam entrance opening 16 of the objective housing 14 and the beam exit opening 12 are each provided with a window that is transparent for low energy x-ray radiation. These windows can also be made, for example, from beryllium or a polymer foil.

A schematically illustrated threaded lock or bayonet lock 11 allows ready exchange of the x-ray objective against a different objective which has, for example, different x-ray optics. In this way, the x-ray camera 1 according to the invention can be easily adapted to a technical application.

For visualizing and documenting the sample, an observation device configured as an optical camera system 50 operating in the visible optical range is associated with the x-ray color camera 1. A digital color camera 51 is used for this purpose. The optical axis of the color camera 51 is deflected by an x-ray-transparent (or mechanically pivotable) mirror 53 into the observation direction of the x-ray color camera 1 or the irradiation direction of the x-ray tube. A fixed deflection mirror 52 is arranged in the beam path to the digital color camera. Substrate materials for x-ray-transmitting mirrors which reflect in the visible spectral range are polyamide, beryllium, Mylar and diamond.

LED elements 42 are arranged in LED sockets 43 on an illumination support 41 for illumination 40 of the sample.

Figure 4A:
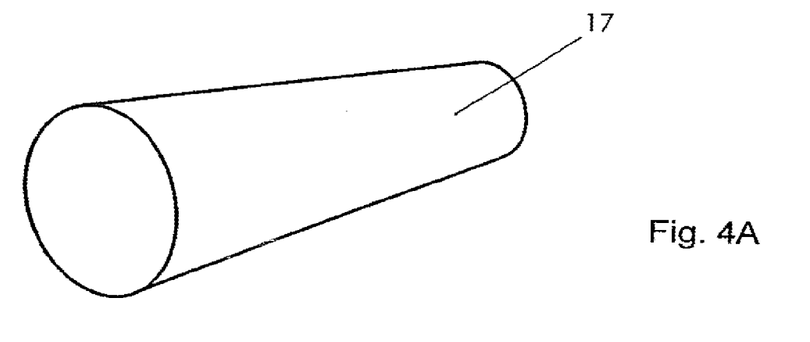
FIG. 4A a perspective view of a capillary structure which is constructed as a magnifying focusing collimator.
Figure 4B:
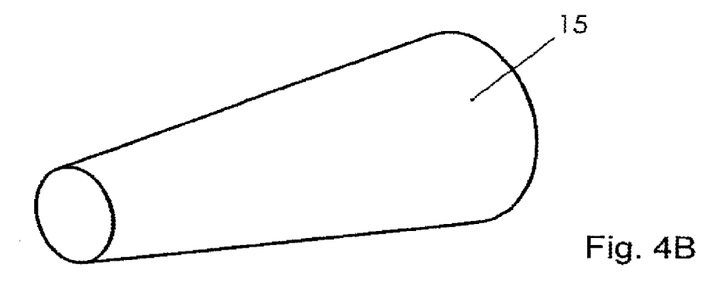
FIG. 4B a perspective view of a capillary structure which is constructed as a reducing focusing collimator.
Figure 4C:
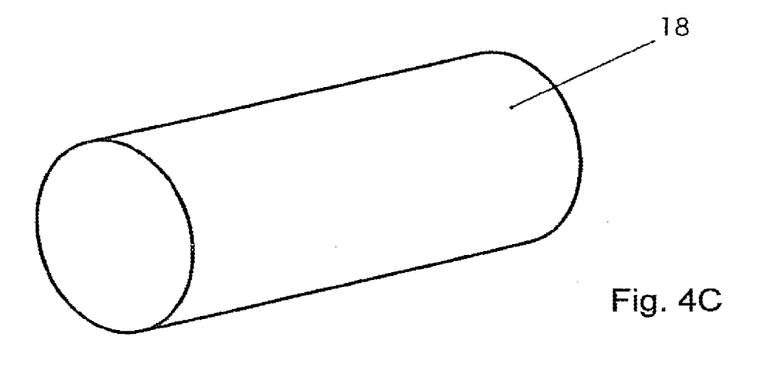
FIG. 4C a perspective view of a capillary structure which is constructed as a parallel focusing collimator.

FIG. 4A shows a perspective view of a capillary structure 17 which is constructed as a magnifying focusing collimator 17. FIG. 4B shows a perspective view of a capillary structure 15 which is constructed as a reducing focusing collimator 15. Lastly, FIG. 4C shows a perspective view of a capillary structure 18 which is constructed as a parallel focusing collimator 18.

The invention claimed is:

1. An x-ray color camera comprising:
a camera housing;
an image pickup element arranged in said camera housing;
said image pickup element having a plurality of image pixel sensors and being sensitive to low-energy x-ray radiation;
said image pickup element being a pn-CCD arrangement and being configured as a two-dimensional pixilated semiconductor sensor;
an objective housing being detachably connected with said camera housing;
said camera housing and said objective housing being gas-tight;
a capillary structure being arranged in said objective housing;
said objective housing and said capillary structure forming an x-ray objective;
said capillary structure being made of glass and being configured to reflect the low-energy x-ray radiation as the low-energy x-ray radiation passes through the capillary structure to be detected by the image pickup element;
said capillary structure being configured as one of a parallel imaging poly-capillary structure, a magnifying imaging poly-capillary structure, and a reducing imaging poly-capillary structure;
said image pickup element and said capillary structure being configured to conjointly generate a spectrally-resolved multi-colored digital x-ray image of an entire sample having spatial and spectral resolution by simultaneously recording, at each of the plurality of image pixel sensors, a spectrum of the low-energy x-ray radiation of the entire sample that passes through the capillary structure of said x-ray objective; and,
wherein each of the plurality of image pixel sensors is configured to capture single x-ray photons, to determine a number of captured single x-ray photons, to determine a photon energy and a wavelength of each single x-ray photon thereby simultaneously determining the spectrum of the low-energy x-ray radiation.

2. The x-ray color camera according to claim 1, wherein the x-ray camera comprises a camera shutter configured for manual operation or for electronic control and having a predetermined or predeterminable aperture opening.

3. The x-ray color camera according to claim 1, wherein the objective housing comprises an interior space, a beam entrance opening and a beam exit opening,
wherein the interior space includes a first space and a second space,
said first space being provided between said beam entrance opening and a first side of said capillary structure,
said second space being provided between said beam exit opening and a second side of said capillary structure, and
wherein each of said beam entrance opening and said beam exit opening are sealed gas-tight by a window which is transparent for low-energy x-rays.

4. The x-ray color camera according to claim 3, wherein the windows of the objective housing are made of beryllium or a thin material which is transparent for low energy radiation.

5. The x-ray color camera according to claim 1, wherein the objective housing is connected with the camera housing by way of a separable threaded lock or a bayonet lock.

6. The x-ray color camera according to claim 3, wherein the interior space of the objective housing is filled with a gas, with the gas being nitrogen or helium or a gas mixture of both.

7. The x-ray color camera according to claim 1, wherein the camera housing is constructed to be gas-tight and has a camera beam entrance opening which is sealed gas-tight by a camera window that is transparent for low-energy x-ray radiation.

8. The x-ray color camera according to claim 7, wherein the camera window is made of beryllium or a thin material which is transparent for low-energy x-ray radiation.

9. The x-ray color camera according to claim 1, wherein an interior space of the camera housing is filled with a gas, with the gas being nitrogen or helium or a gas mixture of both.

10. The x-ray color camera according to claim 1, further comprising a cooling device constructed as a Peltier element, with the cooling device cooling the image pickup element to a temperature in a range from +20° C. to −60° C.

11. The x-ray color camera according to claim 1, wherein the camera housing comprises at least one heat sink.

12. The x-ray color camera according to claim 11, wherein the at least one heat sink comprises a blower.

13. The x-ray color camera according to claim 1, further comprising a data storage device for storing recorded image data,
wherein the data storage device is arranged inside or outside the camera housing.

14. The x-ray color camera according to claim 13, wherein the data storage device is a digital data storage device.

15. The x-ray color camera according to claim 1, further comprising an image processing device for processing recorded image data,
wherein the image processing device is arranged inside or outside the camera housing.

16. The x-ray color camera according to claim 15, further comprising a data transmission interface configured for data exchange with the image processing device.

17. The x-ray color camera according to claim 1, further comprising an observation unit embodied as a digital color camera for visualizing and documenting the sample,
wherein the digital color camera has an optical axis that can be redirected via mirrors.

18. The x-ray color camera according to claim 17, further comprising LED elements for illuminating the sample.

19. The x-ray color camera according to claim 1, wherein the x-ray camera is configured to produce a monochromatic digital x-ray image.

20. A method for recording x-ray images, comprising recording the x-ray images by means of the x-ray color camera as recited in claim 1.

21. The x-ray color camera according to claim 1, wherein each of the plurality of image pixel sensors of the pn-CCD arrangement has a high intensity resolution so that both number and energy of incident single photons can be measured.

22. A method comprising:
arranging an image pickup element in a camera housing;
said image pickup element having a plurality of image pixel sensors and being sensitive to low-energy x-ray radiation;
arranging a capillary structure in an objective housing;
said objective housing and said capillary structure forming an x-ray objective;
said objective housing being detachably connected with said camera housing;
said camera housing and said objective housing being gas-tight;
conjointly generating, by the image pickup element and the capillary structure, a spectrally-resolved multi-colored digital x-ray image of an entire sample having spatial and spectral resolution by:
passing a low-energy x-ray radiation through the capillary structure;

simultaneously recording at each of the plurality of image pixel sensors a spectrum of the low-energy x-ray radiation of the entire sample that passes through the capillary structure of said x-ray objective; and, at each of the plurality of image pixel sensors, capturing single x-ray photons, determining a number of captured single x-ray photons, determining a photon energy and a wavelength of each single x-ray photon thereby simultaneously determining the spectrum of the low-energy x-ray radiation.

23. The method according to claim 22, further comprising:

providing said objective housing with an interior space, a beam entrance opening and a beam exit opening;

said interior space including a first space and a second space;

said first space being provided between said beam entrance opening and a first side of said capillary structure;

said second space being provided between said beam exit opening and a second side of said capillary structure; and gas-tight sealing each of said beam entrance opening and said beam exit opening by a window which is transparent for low-energy x-rays.

* * * * *